(12) United States Patent
Zhou et al.

(10) Patent No.: US 12,144,877 B2
(45) Date of Patent: Nov. 19, 2024

(54) GRAPHENE-BASED MULTIFUNCTIONAL COSMETIC COMPOSITIONS

(71) Applicant: Northwestern University, Evanston, IL (US)

(72) Inventors: Lingye Zhou, Evanston, IL (US); Jiaxing Huang, Wilmette, IL (US); Chong Luo, Evanston, IL (US)

(73) Assignee: Northwestern University, Evanston, IL (US)

( * ) Notice: Subject to any disclaimer, the term of this patent is extended or adjusted under 35 U.S.C. 154(b) by 436 days.

(21) Appl. No.: 17/467,705

(22) Filed: Sep. 7, 2021

(65) Prior Publication Data

US 2021/0401689 A1    Dec. 30, 2021

Related U.S. Application Data

(62) Division of application No. 16/163,182, filed on Oct. 17, 2018, now abandoned.

(60) Provisional application No. 62/573,775, filed on Oct. 18, 2017.

(51) Int. Cl.
| | | |
|---|---|---|
| *A61K 8/19* | (2006.01) | |
| *A61K 8/67* | (2006.01) | |
| *A61K 8/73* | (2006.01) | |
| *A61Q 5/10* | (2006.01) | |

(52) U.S. Cl.
CPC ............. *A61K 8/19* (2013.01); *A61K 8/676* (2013.01); *A61K 8/736* (2013.01); *A61Q 5/10* (2013.01)

(58) Field of Classification Search
None
See application file for complete search history.

(56) References Cited

U.S. PATENT DOCUMENTS

2004/0115232 A1*   6/2004   Giroud ................. A61K 8/19
                                                                424/401

FOREIGN PATENT DOCUMENTS

| CN | 102995394 A |   | 3/2013 | |
|---|---|---|---|---|
| CN | 103191030 | * | 7/2013 | |
| KR | 20130134580 | * | 12/2013 | |
| WO | WO 2015/160764 | * | 10/2015 | ............. C08K 3/042 |

OTHER PUBLICATIONS

Ordikhani et al. (Carbon, 84, 91-102, 2015) Physicochemical and biological properties of electrodeposited graphene oxide/chitosan films with drug-eluting capacity.*
Zhang et al. (Chem. Commun., 2010, 46, 1112-1114) Reduction of graphene oxide vial-ascorbic acid.*
First Office Action issued by the China National Intellectual Property Administration on Oct. 21, 2022 for Chinese patent application No. 201880075623.1; pp. 1-6.
English translation of second Chinese Office Action dated Mar. 17, 2023 issued for Chinese Application No. 201880075623.1; pp. 1-8.

* cited by examiner

*Primary Examiner* — Tigabu Kassa
(74) *Attorney, Agent, or Firm* — Bell & Manning, LLC

(57) ABSTRACT

Cosmetic compositions, including hair coloring compositions, comprising graphene oxide (GO), reduced graphene oxide (r-GO), or both, and water are provided.

17 Claims, 9 Drawing Sheets

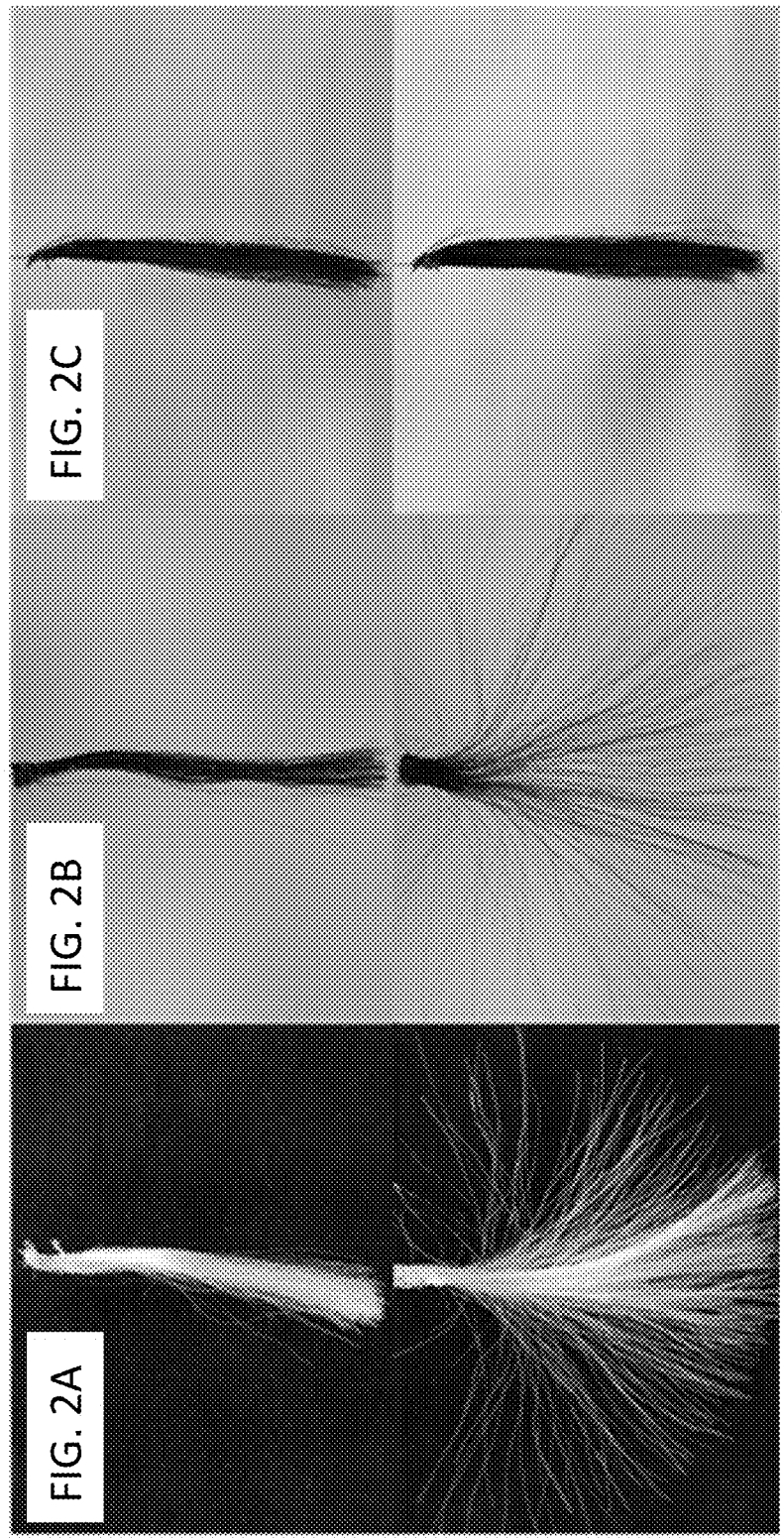

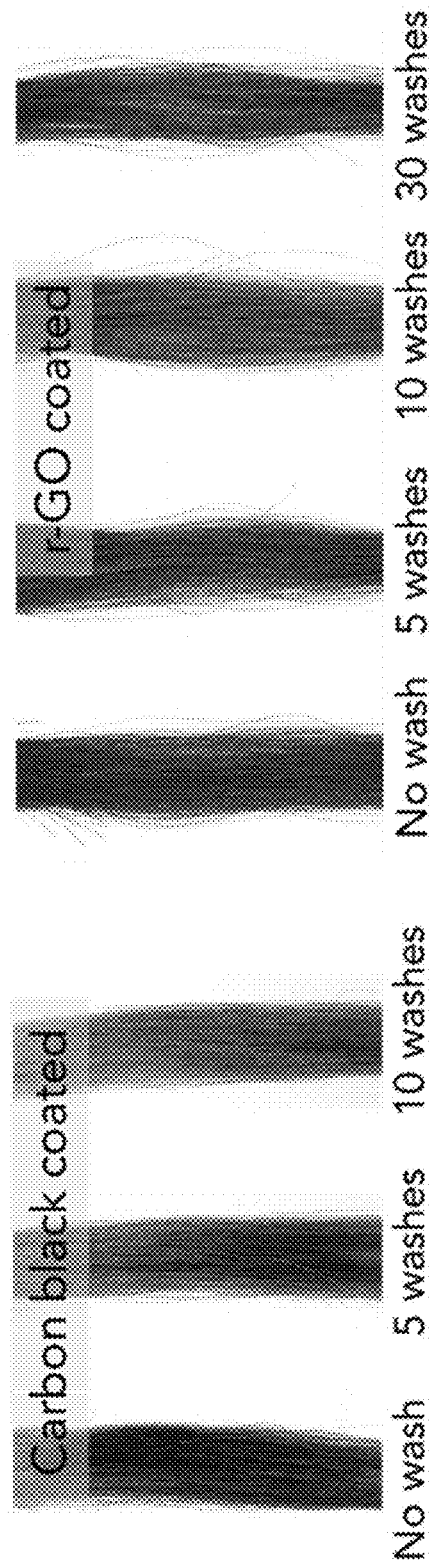

GRAPHENE-BASED MULTIFUNCTIONAL COSMETIC COMPOSITIONS

CROSS-REFERENCE TO RELATED APPLICATIONS

The present application is a divisional of U.S. patent application Ser. No. 16/163,182 filed on Oct. 17, 2018, the entire contents of which are hereby incorporated by reference; which claims priority to U.S. provisional patent application No. 62/573,775 filed on Oct. 18, 2017, the entire contents of which are hereby incorporated by reference.

BACKGROUND

Hair dyes are widely used for altering the cosmetic appearance of hair. The color of hair is determined by the abundance and relative concentrations of melanin pigments, the degradation of which results in grey or white hair.[1,2] The majority of hair dye products permanently change the hair color by a series of oxidative, dye-forming chemical reactions under alkaline conditions.[1,3] The process typically involves the use of a base (e.g., ammonia) to swell and open up the cuticle scales on the hair surface, so that aromatic amine and/or phenol-based colorants (e.g., para-phenylenediamine and para-aminophenol) can penetrate deeply inside the hair. An oxidant (e.g., hydrogen peroxide) is also needed to bleach the natural melanin pigments and to initiate reactions between the colorants to synthesize the final dye compounds.[1] Since the entire process is typically diffusion-limited, it can take hours to complete. Many of these molecular ingredients are toxic, and some are even carcinogenic.[3] If they are absorbed through the skin or inhaled, they could cause allergic reactions,[4-6] or even more severe consequences.[7-12] Treating hair with a weaker alkaline base or at near-neutral pH avoids the opening of the cuticles, and is less likely to inflict permanent hair damage. However, this limits the diffusion of colorants, leading to insufficient loading or semi-permanent to temporary coloration that can be reversed after a few washes.[13]

SUMMARY

Provided are graphene-based cosmetic compositions, including hair coloring compositions. A cosmetic composition may comprise graphene oxide (GO), reduced graphene oxide (r-GO), or both; a water dispersible polymer; and water. A method of using a cosmetic composition may comprise applying a cosmetic composition comprising graphene oxide (GO), reduced graphene oxide (r-GO), or both; a water dispersible polymer; and water, to a keratin-based substrate to form a coating of the composition thereon and drying the coated substrate.

In embodiments, a cosmetic composition comprises graphene oxide (GO), reduced graphene oxide (r-GO), or both; a water dispersible polymer; and water. In embodiments, the composition provides a coating on a keratin-based substrate to which the composition is applied after applying the composition to the substrate, rinsing the coated substrate, and drying the coated substrate. In embodiments, the coating of the coated substrate has an average thickness of at least 1 µm and the average thickness varies by no more than ±10% across the surface of the coated substrate. In embodiments, the composition is a hair coloring composition which changes a lightness (L*) value of the hair to which the composition is applied after applying the composition to the substrate, rinsing the substrate, and drying the substrate. In embodiments, the composition comprises the r-GO and the r-GO is chemically reduced GO. In embodiments, the composition comprises the GO. In embodiments, the composition comprises both the GO and the r-GO and the r-GO is chemically reduced GO. In embodiments, the water dispersible polymer is a compound which is soluble in water below a pH of 7 but which is insoluble in water above a pH of 7. In embodiments, the water dispersible polymer comprises amine groups. In embodiments, the water dispersible polymer is chitosan. In embodiments, the composition comprises a second type of dispersant. In embodiments, the second type of dispersant is an acid. In embodiments, the second type of dispersant is ascorbic acid. In embodiments, the composition comprises an amount of r-GO selected to provide a predetermined L* value to hair to which the composition is applied using a predetermined application procedure. In embodiments, the composition comprises an amount of GO selected to provide a predetermined L* value to hair to which the composition is applied using a predetermined application procedure and after exposure to a predetermined amount of UV radiation or a predetermined amount of heat. In embodiments, the composition comprises an amount of GO and an amount of an additional coloring agent, both selected to provide a predetermined L* value to hair to which the composition is applied using a predetermined application procedure. In embodiments, the composition is free of any other coloring agents besides GO or r-GO. In embodiments, the composition comprises at least 0.01 wt. % of the GO, the r-GO, or both; from 0.1 to 5 wt. % of the water dispersible polymer; from 0 to 10 wt. % of a second type of dispersant; from 0 to 10 wt. % of a co-solvent; from 0 to 10 wt. % of an additional coloring agent; and the water. In some such embodiments, the composition consists essentially of the GO, the r-GO, or both; the water dispersible polymer; the water; optionally, the second type of dispersant; optionally, the co-solvent; and optionally, the additional coloring agent. In embodiments, the composition consists essentially of the GO, the r-GO, or both; the water dispersible polymer; the water; optionally, a second type of dispersant; and optionally, a co-solvent. In some such embodiments, the water dispersible polymer is chitosan and the second type of dispersant is an acid. In embodiments, hair treated with the composition exhibits an L* value after 30 washes which has increased by no more than a factor of 1.75 as compared to an L* value of the treated hair before washing; wherein hair treated with the composition exhibits a surface static voltage after 30 washes which has increased by no more than a factor of 5 as compared to a surface static voltage of the treated hair before washing; or both. In embodiments, hair treated with the composition has a coating of the composition thereon having an average thickness after 30 washes which has decreased by no more than 50% as compared to an average thickness of the treated hair before washing.

In embodiments, a method comprises applying a cosmetic composition comprising graphene oxide (GO), reduced graphene oxide (r-GO), or both; a water dispersible polymer; and water, to a keratin-based substrate to form a coating of the composition thereon and drying the coated substrate. In embodiments, the substrate is hair having an L* value and the coated hair exhibits a changed L* value. In embodiments, the coating of the coated substrate has an average thickness of at least 1 µm and the average thickness varies by no more than ±10% across the surface of the coated substrate. In embodiments, the substrate is hair and the coated hair is curled prior to drying. In embodiments, the method further comprises exposing the coated substrate or a region of the coated substrate to a predetermined amount of UV radiation or a predetermined amount of heat to provide a predetermined L* value for the coated substrate. In embodiments, the method further comprises exposing a plurality of regions of the coated substrate to different predetermined amounts of UV radiation or different predetermined amounts of heat to provide each region with a different predetermined L* value.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 1A shows bundles of blonde hair before and after coating with r-GO/chitosan dye with increasing graphene concentrations, in comparison with another sample treated with a commercial permanent black hair dye. FIG. 1B shows SEM images showing the surfaces of uncoated and coated hair (0.25 wt. %). FIG. 1C shows the lightness of uncoated and graphene coated hairs, and those treated with the commercial permanent black hair dye, measured directly with a fiber optics spectrometer. FIG. 1D show representative stress-strain curves of a strand of hair before and after graphene coating, showing no apparent change in tensile properties.

FIGS. 2A-2D demonstrate the antistatic property of graphene coated hair. FIG. 2A shows strands of uncoated hair, FIG. 2B shows strands of hair treated with a commercial black dye and FIG. 2C shows graphene coated hair before (top row) and after (bottom row) electrostatic charging. The strands are tied with an insulating cotton string on the top. Uncoated hairs and hairs treated with commercial dye cannot dissipate the electrostatic charges, and show strong "flyaway" effect. The antistatic effect of graphene coating (0.25 wt. %) is evident. FIG. 2D shows the surface static voltage of the hair bundles decreased drastically with graphene coatings.

FIGS. 3A-3D demonstrate the durability of graphene coated hair against washing. Images showing bundles of (FIG. 3A) carbon black/chitosan coated and (FIG. 3B) graphene-dyed hair (0.25 wt. %) before and after repeated shampoo washing. FIGS. 3C and 3D compare the corresponding changes in lightness and surface static voltage, respectively. The 2D morphology of r-GO may provide barrier properties that better protect the composite against washing. Additional exhaustive washing tests showed that graphene-coated hair can sustain at least over 30 times of washing (FIG. 3C), which already approaches the performance requirement of commercial permanent hair dyes.

DETAILED DESCRIPTION

Provided are graphene-based cosmetic compositions, including hair coloring compositions. The cosmetic compositions comprise graphene oxide (GO), reduced graphene oxide, or both. The GO and r-GO colorants can be formulated in water without hazardous ingredients or solvents, and applied to hair (including blonde, grey and/or white hair) by spraying or brushing to yield various shades of brown to black colors. They can also sustain vigorous shampoo washing for dozens of times. The GO and r-GO have much better film-forming capabilities and durability as compared to other conventional carbon-based colorants. In addition, embodiments of the graphene-based hair coloring compositions impart a broad range of new optical, electrical, thermal, and biochemical properties to hair, enhancing comfort level and cosmetic performance.

In one aspect, cosmetic compositions are provided. The cosmetic compositions are formulated for topical application to a variety of substrates in order to alter the appearance thereof. The substrates may include keratin-based substrates such as the hair, fur skin, nails, etc. of a mammal, including humans. The term "hair" includes hair anywhere on the human body, e.g., hair on the scalp, eyelashes, eyebrows, etc. In an embodiment, a cosmetic composition comprises graphene oxide (GO), reduced graphene oxide (r-GO), or both and water. In the present disclosure, "graphene-based" refers to compositions comprising GO, r-GO, or both.

The GO/r-GO in the cosmetic compositions is used as a coloring agent. The GO/r-GO is in the form of a plurality of thin, flexible sheets. Each sheet may comprise from one to several (e.g., 3-10) monolayers of GO or r-GO. Thus, the thickness of the sheets may be less than about 10 nm, less than about 5 nm, less than about 1 nm, or in the range of from a monolayer to about 1 nm. The lateral dimensions of the sheets may be on the order of microns, e.g., 1 µm, 10 µm, 50 µm, 100 µm, providing an aspect ratio of at least >1000. The thinness and flexibility of the sheets facilitates the formation of a conformal coating of GO/r-GO on the surfaces of the substrates to which the cosmetic compositions are applied.

Known methods may be used to form the GO and the r-GO of the cosmetic compositions, including the methods described in the Example below (i.e., modified Hummers' method to form GO and chemical reduction of GO via a reducing agent, e.g., ascorbic acid, to form r-GO). In embodiments, the r-GO is chemically reduced GO. Such r-GO is physically and chemically distinguishable from GO which has been reduced by other methods. Such r-GO is also physically and chemically distinguishable from graphene formed by other methods. In embodiments, the r-GO is characterized by a resistivity of $10^4$ ohms/square or less, of $10^5$ ohms/square or less, or in the range of from $10^4$ to $10^5$ ohms/square.

Figure 1A:
FIGS. 1A-1D demonstrate the graphene dyeing of light-colored hair.
Figure 1B:
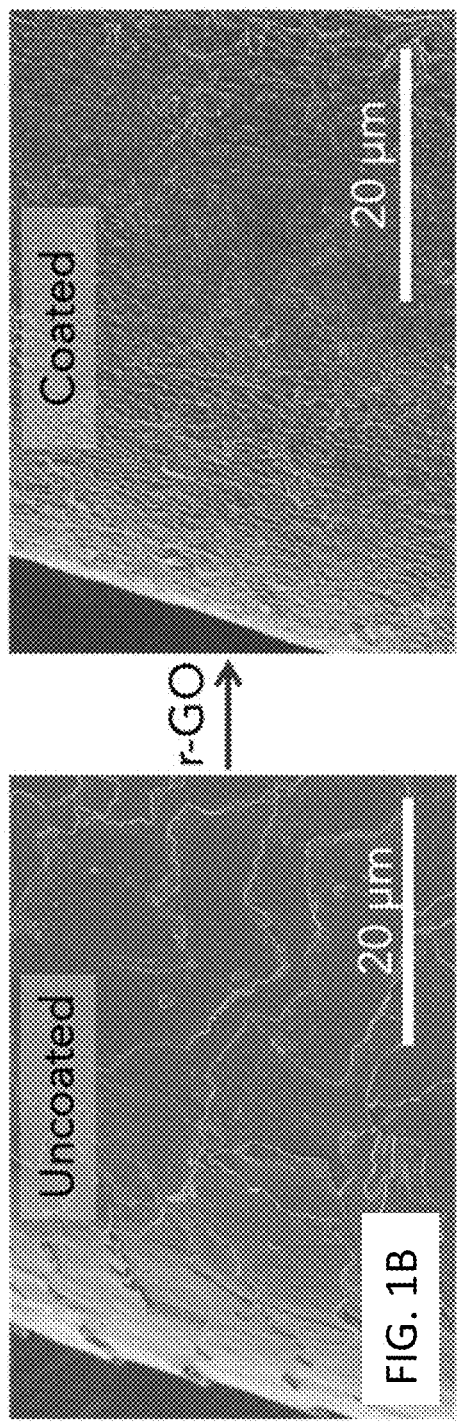
Figures 1C, 1D:
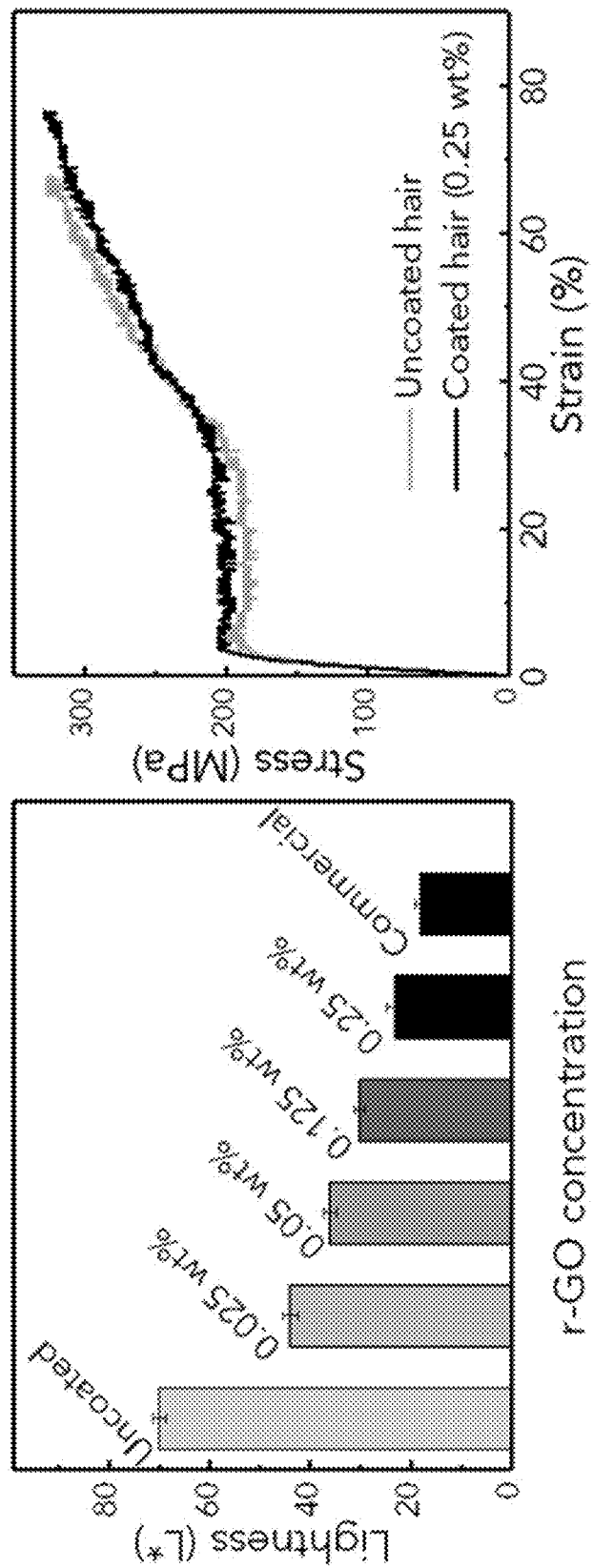

Various amounts of GO/r-GO may be used in the cosmetic compositions, depending upon the desired application and/or the desired properties for the treated substrates. To the human eye and under visible radiation, GO appears transparent, while r-GO appears black. Thus, in embodiments in which the cosmetic composition is used to darken a desired substrate, the composition may include an amount of r-GO selected to provide a desired darkness. By way of illustration, FIG. 1A shows samples of light-colored hair (in this embodiment, blonde hair) onto which a hair coloring composition comprising various amounts of r-GO from 0.025 wt. % to 0.25 wt. % was applied. By "wt. %," it is meant weight of the named component as compared to the total weight of the cosmetic composition. Increasing the amount of the r-GO in the composition resulted in visibly darker colored hair. The darkness may be quantified as a lightness L* value, as measured using a fiber optics spectrometer under the conditions described in the Example, below. In embodiments, the composition comprises an amount of r-GO selected to provide a predetermined lightness value (L*) to a surface of a substrate to which the composition is applied using a predetermined application procedure. The predetermined application procedure may refer to, e.g., combing, brushing, spraying, rubbing, dip-coating, soaking the substrate; waiting a period of time, e.g., 5 minutes; rinsing the coated substrate with water; and drying the coated substrate. The predetermined application procedure may be provided as a set of instructions with the cosmetic composition. In embodiments, the amount of r-GO is selected to provide a L* value of no more than about 40, no more than about 35, no more than about 20, or in the range of from 20 to 40. (See FIG. 1C.)

GO absorbs ultraviolet (UV) radiation, which can convert transparent GO to dark r-GO. Thus, GO may be included in the cosmetic compositions to provide UV protection; the GO of the treated substrates will absorb potentially damaging UV radiation instead of the materials from which the substrate is composed. In embodiments, the cosmetic composition may include an amount of GO selected to provide a desired level of UV protection to the substrate to which the cosmetic composition is applied. The level of UV protection may be quantified as a sun protection factor (SPF), similar to sunscreens. The SPF value may refer to that measured from a 1 µm to 5 µm, e.g., 2 µm, thick layer of the cosmetic composition (after application and drying) using the measurement method described in Dutra, Elizângela Abreu, et al. "Determination of sun protection factor (SPF) of sunscreens by ultraviolet spectrophotometry." *Revista Brasileira de Ciências Farmacêuticas* 40.3 (2004): 381-385, which is hereby incorporated by reference in its entirety. In embodiments, the cosmetic composition includes an amount of GO selected to provide a predetermined SPF value to a surface of a substrate to which the cosmetic composition is applied using a predetermined application procedure. The predetermined application procedure may refer to, e.g., combing, brushing, spraying, rubbing, dip-coating, soaking the substrate; waiting a period of time, e.g., 5 minutes; and drying the coated substrate. The predetermined application procedure may be provided as a set of instructions with the cosmetic composition. In embodiments, the amount of GO is selected to provide a SPF value of at least 10, at least 30, or at least 50.

The UV-absorbing property of GO may also be used to provide an indicator of UV exposure. Specifically, the darkness of a substrate treated with a GO-containing cosmetic composition may be compared to a predetermined calibration chart (correlating darkness to length of UV exposure) in order to determine the length of time the treated substrate must have been exposed to UV light.

The UV-absorbing property of GO may also be used in applications in which different regions of GO-coated substrates are exposed to different amounts of UV-radiation (e.g., different intensities or exposure times) in order to provide a substrate having different levels of darkness in the different regions. The UV-exposure may be controlled and/or combined with masks/filters to achieve any number of predetermined patterns, e.g., the gradient or "ombre" effect shown in FIG. 4A. Since GO may also be converted to r-GO by using heat, patterning a substrate with different levels of darkness in different regions thereon may be carried out using heat instead of UV-radiation. In addition, the cosmetic composition may comprise an amount of GO selected to provide a predetermined L* value to a surface of a substrate to which the cosmetic composition is applied using a predetermined application procedure (see above) and after exposure to a predetermined amount of UV radiation (e.g., exposure to a UV lamp for 1, 2, 3, 5, 10 hours) or a predetermined amount of heat (e.g., exposure to a hair drier for 5, 20, 30, 45, 60 minutes). The predetermined application procedure/amount of UV radiation/amount of heat may be provided as a set of instructions with the cosmetic composition.

In embodiments, the amount of r-GO in the cosmetic composition is in the range of from 0 to about 1 wt. %. In embodiments, the amount of GO in the cosmetic composition is in the range of from 0 to about 1 wt. %. In both cases, this includes amounts in the range of from about 0.1 wt. % to about 0.75 wt. %, or from about 0.2 wt. % to about 0.5 wt. %. In embodiments, the only coloring agents used in the cosmetic composition are GO and r-GO; i.e., the composition is free of any other coloring agents. By "free" it is meant that the amount of other coloring agents may not be perfectly zero, but that the amount of other coloring agents is so small so as to have no measurable coloring effect in the composition. In embodiments, the only coloring agent used in the composition is GO, r-GO, or both GO and r-GO.

The cosmetic compositions may also include a dispersant selected to facilitate dispersion of the GO/r-GO within the water. The dispersant may also be selected to facilitate the binding of the GO/r-GO to the substrate to which it is applied. Water dispersible or water soluble polymers may be used as dispersants, e.g., polyvinylpyrrolidone, polyvinyl alcohol, polyethylene glycol, and polysaccharides, e.g., starch. Sucrose, glucose, keratin, acrylic acid, and cysteine may also be used as dispersants. In embodiments, the dispersant is a compound which is soluble in water below a pH of 7 (e.g., pH of 1, 2, 3, 4, 5, 6), but which is insoluble in water above a pH of 7 (e.g., 8, 9, 10, 11, 12, 13, 14). In embodiments, the dispersant is a water dispersible polymer comprising amine groups. In embodiments, the dispersant is chitosan. Water dispersible or water soluble polymers capable of strongly adhering to hair and to GO or to r-GO simultaneously through hydrogen bonding, pi-pi stacking and/or forming covalent bonds, such as other polysaccharides, or other amine-containing polymers or short chain oligomers, including conducting polymer polyanilines and non-conducting, amine-containing polyelectrolytes may be used. As shown in the Example, below, in certain cosmetic compositions comprising both GO/r-GO and chitosan, the GO/r-GO and chitosan function synergistically to provide a uniform and durable coating on hair.

More than one type of dispersant may be used. In embodiments, ascorbic acid (an acid dispersant) may be included in the cosmetic composition as a second type of dispersant, i.e., a co-dispersant. Other such co-dispersants include acetic acid, formic acid and hydrochloric acid. Other of the water dispersible/soluble polymers as described above may be used as a co-dispersant.

Various amounts of the dispersant/co-dispersant may be used. In embodiments, the amount of a first type of dispersant is in the range of from about 0.1 wt. % to about 1 wt. %. This includes embodiments in which the amount of a first type of dispersant is in the range of from about 0.2 wt. % to about 0.75 wt. % or from about 0.4 wt. % to about 0.6 wt. %. In embodiments, the amount of a second type of dispersant is in the range of from about 1 wt. % to about 10 wt. %. This includes embodiments in which the amount of a second type of dispersant is in the range of from about 2 wt. % to about 8 wt. % or from about 4 wt. % to about 6 wt. %.

In embodiments, the cosmetic composition is free of a hair binding peptide, including the hair binding peptides disclosed in U.S. Pat. No. 7,452,528, which is hereby incorporated by reference for its disclosure of hair binding peptides. In embodiments, the cosmetic composition is free of a diethylene triamine copolymer, a polymeric quaternary ammonium salt, and a quaternized polyvinyl pyridine.

The cosmetic compositions may also include other additives depending upon the application. Illustrative additives include those generally found in cosmetic compositions formulated for use on hair, skin, nails, e.g., hair coloring compositions, hair shampoos, hair conditioners, hair spray, hair gel, hair mousse, sunscreen, make-up, lotion, nail polish, etc. However, at least some embodiments of the cosmetic compositions are characterized by the absence of ingredients found in certain conventional cosmetic compositions, e.g., conventional hair coloring compositions. These include bases (e.g., ammonia), oxidants (e.g., peroxides), and other coloring agents (e.g., para-phenylenediamine, para-aminophenol, pigments such as carbon black, carbon-based colorants such as carbon nanotubes). In embodiments, the cosmetic composition is free of such components. The term "free" has a meaning analogous to that described above.

In embodiments, the cosmetic compositions may include other coloring agents besides GO/r-GO. Such other coloring agents include molecular dyes or pigment particles, including dyes/pigments typically used in temporary and semi-permanent hair coloring compositions. Illustrative dyes/pigments include conducting polymer polyaniline (naturally blue, but turns green in the presence of an acid), rhodamine 6G (red), Coomassie violet 8200 (purple). This list is not exhaustive as any dye/pigment may be used. As shown in the Example, below, the GO/r-GO extends the durability of the treated substrate against washing, effectively converting a temporary or semi-permanent dye/pigment into a more permanent one. Without wishing to be bound to any particular theory, the two-dimensional and flexible morphology of GO/r-GO may act as a barrier to protect the other coloring agents against washing, making the colorization effect last longer. In embodiments, the cosmetic composition may include a non-graphene, two-dimensional material, e.g., a clay. The combination of GO/r-GO with molecular dyes/pigments also provides the treated substrate with additional antistatic and/or chromic properties. The cosmetic composition may comprise an amount of GO/r-GO/additional colorant selected to provide a predetermined L* value to a surface of a substrate to which the cosmetic composition is applied using a predetermined application procedure (see above).

The balance of the cosmetic composition is made up of water, i.e., the cosmetic compositions are aqueous in nature. The water content is generally greater than about 50 wt. %, 60 wt. %, 75 wt. %, 85 wt. %, or 95 wt. %. Co-solvents, e.g., a short chain alcohol such as ethanol, may be used but are not required.

An illustrative hair coloring composition comprises at least 0.01 wt. % of GO, r-GO, or both; no more than 5 wt. % of a dispersant; no more than 10 wt. % of a co-dispersant; no more than 10 wt. % of a co-solvent; from 0 wt. % to 10 wt. % of an additional colorant; and water. Regarding the amounts of these components, other amounts such as those described above may be applied to provide other illustrative hair coloring compositions. In embodiments, the hair coloring composition consists essentially of or consists of these components.

In another aspect, the present disclosure provides methods of using the cosmetic compositions described herein. In an embodiment, such a method comprises applying the cosmetic composition to a surface of a desired substrate to form a coating of the cosmetic composition thereon. The application may be carried out in various ways including combing, brushing, spraying, rubbing, dip-coating, soaking, etc. The method may further comprise drying the coated substrate. The drying may be in air or may be facilitated by using heat. The drying may be carried out for a period of time and at a temperature selected to remove water from the coating and/or to provide a desired darkness of the coated substrate (e.g., when converting GO to r-GO using heat). Similarly, the method may further comprise exposing the coated substrate to UV radiation under conditions (e.g., wavelength, intensity, time) to provide a desired darkness of the coated substrate. The method may further comprise the step of washing the coated substrate with water (or a cleaning composition such as a shampoo) to remove excess colorant. In embodiments, however, the drying step is carried out without first washing with water or a cleaning composition. In embodiments, the coated substrate is curled (including bending, twisting, etc.) prior to drying.

In another aspect, the present disclosure provides substrates which have been treated with the cosmetic compositions described herein. Illustrative substrates have been listed above and include hair, e.g. human hair. Treated hair may characterized by the thickness of the graphene-based coating thereon. In embodiments, the coating has an average thickness of at least about 1 μm, at least about 2 μm, at least about 3 μm, or in the range of from about 1 μm to about 5 μm. By "average" thickness it is meant an average over a representative number of hairs. The average thickness may be determined from scanning electron microscope (SEM) images of cross-sections of coated hairs. Treated hair may be characterized by the uniformity of the graphene-based coating thereon. In embodiments, the coating has an average thickness that does not deviate by more than about ±10%, about ±5%, or about ±2% along the length of the hair from one end to an opposing end. Uniformity may also be determined from SEM images of treated hair. (See FIG. 1B.) Embodiments of the present cosmetic compositions provide darker and more uniform coatings as compared to hair treated with carbon particle-based compositions from corresponding dyes with the same loading levels, between 0.025 to 0.25 wt. %.

At least some embodiments of the present cosmetic compositions provide treated hair with increased antistatic properties and/or increased thermal conductivity as compared to untreated hair. The antistatic properties of hair may be quantified by measuring the surface static voltage of the hair using a surface DC voltmeter under the conditions and using the application method described in the Example, below. Treated hair may be characterized by a surface static voltage that is at least 6 times lower than untreated hair, at least 10 times lower, at least 50 times lower, or at least 100 times lower. The amount of GO/r-GO in the cosmetic composition may be selected to provide a desired antistatic performance. (See FIG. 2D.) The thermal conductivity of hair may be quantified by measuring the heating or cooling rate of hair using an infrared (IR) camera under the conditions and using the application method described in the Example, below. Treated hair may be characterized by a heating/cooling rate that is at least 2 times faster, at least 3 times faster, or at least 5 times faster than untreated hair.

Treated hair may also be characterized by its durability, i.e., its resistance to a change in a property after washing. The durability may be quantified by measuring the L* value of the treated hair (treated as per the application method described in the Example, below) after washing (under the conditions described in the Example, below). In embodiments, the treated hair exhibits an L* value after a predetermined number of washes (e.g., 5, 10, 15, 20, 25, 30, 35) which has increased by no more than a factor of 1.75, 1.70, 1.65, or 1.60 as compared to an L* value of the treated hair before washing. (See FIG. 3B, 3C.) The durability may be quantified by measuring the surface static voltage of the treated (treated as per the application method described in the Example, below) after washing (under the conditions described in the Example, below). In embodiments, the treated hair exhibits a surface static voltage after a predetermined number of washes (e.g., 5, 10, 15, 20, 25, 30, 35) which has increased by no more than a factor of 5, 4, 3, or 2 as compared to a surface static voltage of the treated hair before washing. (See FIG. 3D.) The durability may also refer to a resistance to a change in other properties, e.g., coating thickness, coating uniformity, coating coverage (measurable via SEM), curvature, etc. In embodiments, the average thickness of the coating of the treated hair (treated as per the application method described in the Example, below) after a predetermined number of washes under the conditions described in the Example, below (e.g., 5, 10, 15, 20, 25, 30, 35) has not decreased by more than 50% as compared to the average thickness of the treated hair before washing. This includes decreases of no more than 40%, 30%, or 20%.

By contrast to conventional hair coloring compositions, hair coloring compositions provided herein are significantly less damaging to hair. This may be quantified by measuring the tensile properties of treated hair using a mechanical analyzer under the conditions described in the Example, below. In embodiments, the treated hair exhibits a tensile stress-strain curve which is about the same (e.g., does not deviate by more than 10%) as a tensile stress-strain curve of untreated hair. (See FIG. 1D.)

Example

Introduction

This Example demonstrates that graphene-based sheets are found to be excellent hair dyes. Using graphene oxide (GO) and its reduced form r-GO, water-based formulations can be obtained to form smooth and continuous coatings on hair. This not only avoids the use of toxic, small molecular ingredients in common black hair dyes, but also renders new properties of hair for enhanced comfort, such as greatly improved antistatic performance and heat dissipation. After drying, the graphene hair dyes can form a strongly adhering coating on hair surfaces, which can resist repetitive shampoo washing, reaching the performance requirement of permanent hair dyes. The color of the GO coating can be gradually darkened or patterned to create the effect of gradient dyeing, and the lightness of the resulting r-GO coating can be adjusted through loading level to produce different shades.

Experimental

Preparation of GO and r-GO dyes

GO was prepared through a modified Hummers' method[19] and purified with two-step washing.[51] GO (5 mg/mL in water, 10 mL) was then reduced with ascorbic acid (5 wt %, 10 mL) under stirring and heating at 90° C. for 1 hour. The resulting black r-GO product was washed 3 times with DI water through exhaustive centrifugation (10000 rpm, 5 min). Next, 50 mg of chitosan (Sigma-Aldrich, medium molecular weight) was dissolved in 20 mL of warm ascorbic acid solution (60° C., 2.5 mg/mL) to create a chitosan gel, in which the sheets were better dispersed. Chitosan gel also improves the adhesion to the hair surface. GO- and r-GO based formulations were prepared by mixing the sheets with chitosan at various loading levels.

Hair Dyeing with GO and r-GO

Human hair samples (Emosa, #60 platinum blonde) were first thoroughly washed with water to remove any existing surface coating. The as-prepared dye solutions were sprayed onto hair and combed to yield a visually uniform coating, then dried in air or using a commercial hair dryer. The entire dyeing process can be completed within 10 minutes. Ombre dyeing was achieved by UV irradiation of GO coated hair with gradient dose along the length of the hair. It can also be achieved by applying a gradient of heating using a hair dryer.

Durability Test of Graphene Hair Dye

Bundled hair coated with r-GO/chitosan was soaked in 5 vol. % of shampoo (Pantene Pro-V) in 40 mL of water sealed in a 50 mL centrifugation tube (Falcon). The tube was then horizontally fixed on a vortex mixer and vigorously shaken for 5 minutes. The frequency is determined to be about 10-12 Hz by counting the tube's movement from a recorded video. After washing, the hair was rinsed with water and dried in air or at 60° C. The r-GO/chitosan coating can sustain over 30 washes without significant decoloration.

Characterization

The lightness of hair (L*),[52] which is an indicator of the darkness of hair was measured directly using a Jaz fiber optics spectrometer (Ocean Optics Inc.). The spectrometer was first calibrated with a hemispherical reflectance black standard and printer paper (92 bright). The L* measured from the printing papers was set to be 100, and L* from the black standard was set to be 0. The original lightness of the blonde hair was measured to be around 75. For every sample, lightness was measured 10 times to calculate the average value.

The surface static voltage was measured using a surface DC voltmeter (SVM2, Alphalab, Inc.) Electrostatic charges were induced by rubbing a Scotch® polypropylene sheet against a strand of hair for 10 times, which was tied and suspended with an insulating cotton thread. A surface DC voltmeter was placed 1 inch away from the sample to record the induced static voltages. For every sample, 5 measurements were made to calculate the average value.

To compare heating and cooling rates, 250 strands of hair were fixed across a rectangular frame. The middle part (ca. 5 cm) of the hair was suspended to allow direct contact with a heating stage. The strands were arranged so that both types of hair have similar packing density and apparent thickness on the frame. IR images and temperatures of the hair were recorded using an IR camera (Optotherm, InfraSight MI320). For heating, the hair samples were placed on top of a heating element set at 34° C., the typical temperature of human skin, right before IR recording. For cooling, the hair samples were first heated to the same temperature of 36° C., and the heating element was removed immediately before IR recording. Room temperature during the experiments was around 24° C.

SEM images were taken on a Hitachi SU8030 scanning electron microscope. The tensile tests were performed using a mechanical analyzer (ElectroForce 5500, BOSE).

Results

Graphene-Based Aqueous Black Hair Dye

Blonde hair samples were used to test the performance of graphene dyes. The typical composition of the dye solutions includes r-GO sheets as the colorants, chitosan polymer as the dispersing agent[31,32] and vitamin C (i.e., ascorbic acid) as the co-dispensing agent, which was also used to reduce GO. The atomic force microscopy (AFM) images showed that the lateral dimensions of GO sheets are a few microns, with a thickness of around 1 nm. After reacting with ascorbic acid, GO sheets in the brown colloidal dispersion turned into black r-GO sediment. Chitosan was utilized as a dispersing agent for r-GO and a binder to improve the adhesion of the graphene hair dye. Since they are well dispersed in water, both GO and r-GO/chitosan dispersions can easily form uniform coatings on a surface by drop casting. The UV-Vis spectra obtained show that r-GO indeed has much stronger absorption than GO in both the UV and visible range of wavelengths, due to partial restoration of the conjugated carbon network after reduction. This is a much simpler and safer formulation than organic hair dyes, as it does not contain any toxic molecular specifies or volatile components. The water-based dye solution can be directly applied to hair by spraying and/or combing to generate a uniform coating, without the need for any pre-treatment. After drying the r-GO dye in air or with a hair dryer, the color of the hair turned into a uniform shade of black. This coating-based dyeing process can be completed in less than 10 minutes, which is much faster than using diffusion-based molecular hair dyes.

Figure 2D:
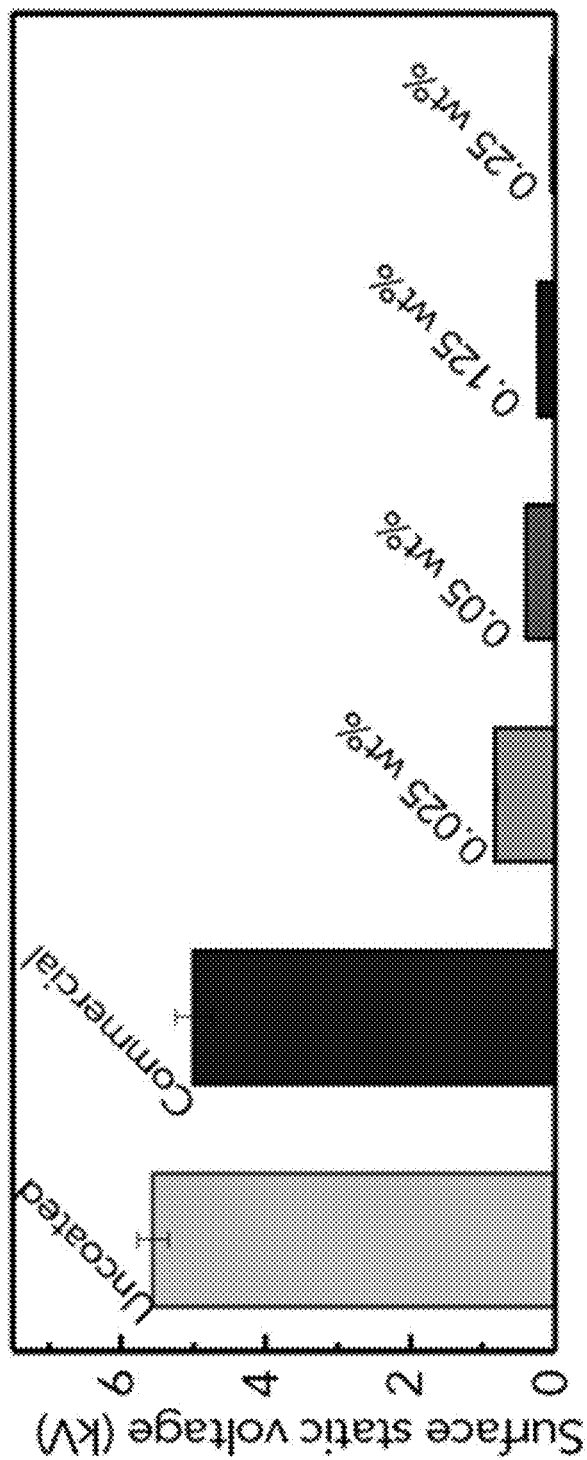

As shown in FIG. 1A, gradient shades of black can be achieved by varying the concentration of graphene in the dye solution from 0.025 to 0.25 wt. %. Observation under the scanning electron microscope (SEM) showed that the surface of hair has been uniformly coated by a layer of graphene/chitosan (FIG. 1B) without any obvious aggregation or scaling. The thickness of the graphene layer was found to be typically around 2 µm. The difference in hair darkness was quantified by lightness measurements based on optical reflectance (FIG. 1C), which suggests that the lightness of r-GO coated hair can be continuously decreased by increasing the loading of r-GO. It was found that 0.025 wt. % graphene dispersion started to yield a visually uniform coating on hair, and the 0.25 wt. % dispersion already dyed the hair in dark black, approaching the appearance and lightness rendered by a commercial black hair dye. In conventional hair dyeing, the cuticles must be opened to allow the diffusion and reaction of colorants inside hair. This significantly degrades the hair's mechanical properties, which may not fully recover afterward. In contrast, the graphene coating does not react with hair and does not weaken the hair based on the results of tensile tests (FIG. 2D).

Antistatic Performance

Figure 3D:
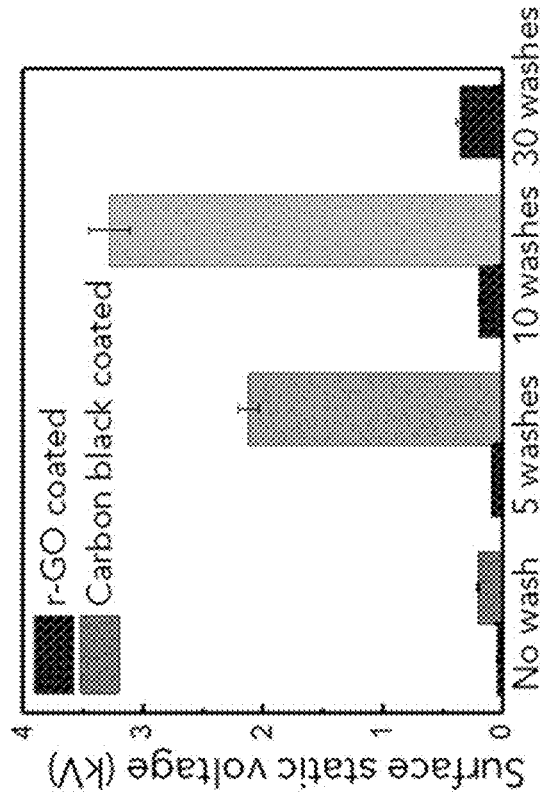
Figure 3C:
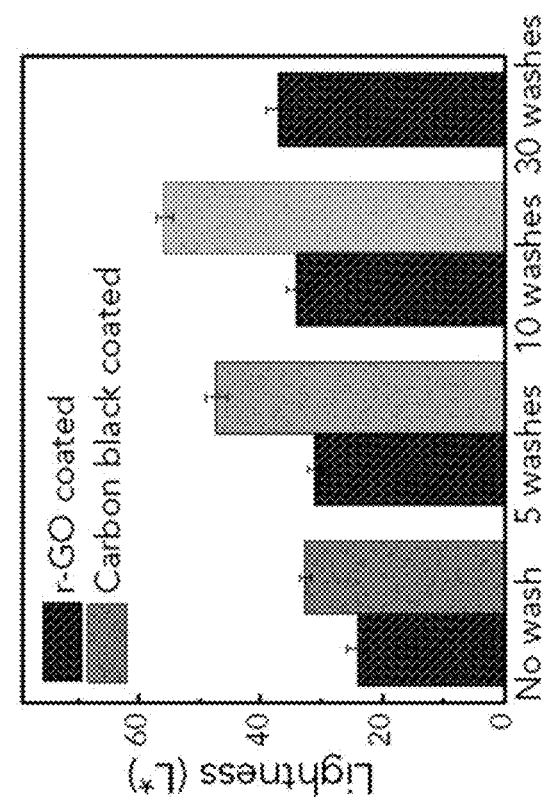

Hair is insulating and cannot easily dissipate electrostatic charges generated by the triboelectric effect, especially in cold and dry weather.[33] Charged hair strands repel each other and can even stand up on their ends, creating an uncomfortable "flyaway" effect.[15,33] Molecule-based hair dyes tend to lift up and loosen the seal between the cuticle scales, making it harder for hair to lock moisture and discharge. With their electrical conductivity, graphene-based coatings can very effectively dissipate electrostatic charges on hair. Both uncoated hair (FIG. 3A) the hair treated with the commercial black dye (FIG. 3B) exhibited a drastic response to charging, induced by rubbing with a plastic film. In contrast, the graphene coating rendered hair excellent antistatic performance to avoid static build up (FIG. 3C). The surface static voltages on rubbed hair were measured using a surface DC voltmeter. FIG. 3D shows that rubbing induced a surface static voltage of around 5 kV for both the uncoated hair and hair treated with commercial dye, and only about 0.8 kV and 0.05 kV for hair treated with 0.025 and 0.25 wt. % of graphene dye, respectively. The r-GO coating used in this work was only lightly reduced by ascorbic acid to render black color, and typically has a resistivity on the order of $10^4$ to $10^5$ ohms/square, which is already sufficient for antistatic purposes.[34]

Improved Thermal Conduction

Hair is an important part of an intricate system that regulates body temperature. Improving the thermal conductivity of hair can improve its thermoregulation performance, such as faster heat dissipation from the head for increased comfort. Coating graphene on hair led to its improved thermal conductance. This was tested by comparing the heating and cooling rates of uncoated, graphene-coated hair and hair treated with commercial dye. All samples were first brought into contact with a heating element set at 36° C., a typical temperature of the human skin. Photos taken by an infrared (IR) camera during heating showed a faster overall temperature increase for graphene-coated hair, which was already more than 3° C. warmer than both the uncoated hair and hair treated with commercial dye within the first 3 seconds of heating. Next, all hair samples were preheated to 36° C., after which the heating element was removed. The snapshots taken with the IR camera show that graphene-coated hair samples also dissipated heat faster. Within 3 seconds of cooling, the overall temperature of graphene-coated hair was already 3° C. lower than those of the other two samples, reaching room temperature more quickly. This temperature difference is already sufficiently significant to be felt by human skin, and it should help to prevent local heat buildup in skin to increase the level of comfort.

Durability of Graphene Coating

Although graphene hair dye does not change hair color through chemical reactions, the graphene/chitosan coating strongly adheres to hair after drying and cannot be easily washed off. This is attributed to the following factors: First, GO and r-GO sheets are highly flexible due to their high aspect ratio, and they can strongly interact with chitosan through hydrogen bonding.[36,37] This soft sheet-like shape also helps to yield a thin and uniform composite coating after drying. Next, chitosan can bind strongly with and keratin, the key structural protein at the surface of hair, through its amino and hydroxyl groups. More interestingly, chitosan is insoluble in water under near neutral to basic conditions, but becomes soluble in the presence of weak acid such as ascorbic acid.[40] When excess ascorbic acid is rinsed off after hair dyeing, the r-GO/chitosan coating becomes insoluble. These properties of chitosan make it a very suitable binder for graphene-based hair dyes.

Exhaustive shampoo washing tests were conducted for hairs treated with r-GO/chitosan, in comparison with those treated with carbon black/chitosan coating. Carbon black powders are chosen as a control. As shown in the images in FIG. 3A, the color of hair coated with carbon black powders faded away after only 5 shampoo washes and turned light gray after 10 washes. However, the color of r-GO coated hair still remained black after washing with shampoo over many times (FIG. 3B), which is confirmed by lightness measurements (FIG. 3C). The sheet-like shape of r-GO makes it an effective barrier against water penetration, which may make the coating more resistant to washing. Moreover, while the antistatic performance of carbon black coated hair rapidly degrades upon washing, graphene coated hair retains its excellent antistatic properties even after exhaustive washing for 30 times (FIG. 3D). Commercial permanent hair dyes generally are not affected by washing since the chemical reactions changes the composition of the hair. However, they also need to be re-applied, typically after about one month or 30 washes due to hair growth.[2] r-GO/chitosan coated hair can resist at least 30 shampoo washes without significant degradation in color and antistatic properties. Therefore, the durability of such graphene hair dyes is already sufficient to render a "permanent" coloring effect.

Ombre Hair Dyeing with GO

Figure 4A:
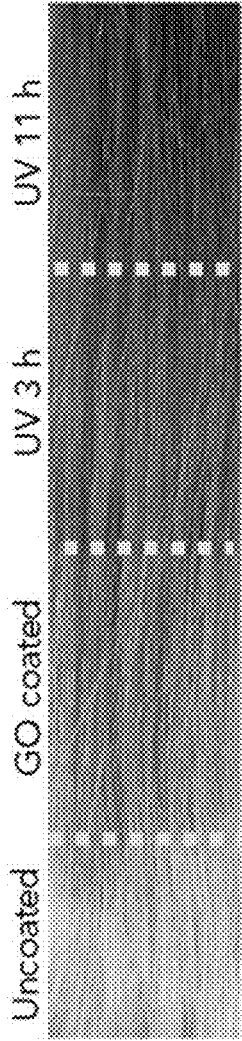
FIGS. 4A-4B demonstrate gradient dyeing using GO/chitosan triggered by UV irradiation. Gradient coloring (FIG. 4A) and reduction in lightness (FIG. 4B) can be achieved by controlling the duration of UV irradiation on different segments of GO/chitosan coated hair (0.25 wt. % of GO in the dye solution).
Figure 4B:
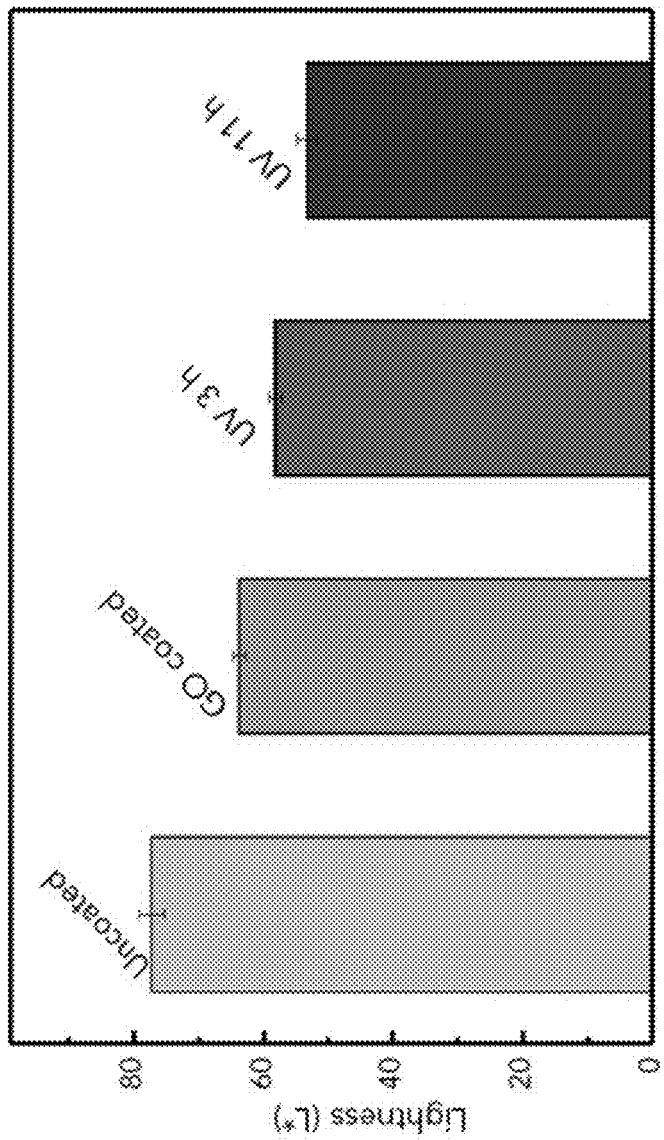

Gradient hair dyeing, also known as "ombre", has recently grown in popularity. This is usually done by applying more than one hair dye along the length of the hair strands, which requires more sophisticated control over timing and colorant compositions during dyeing procedures. Since GO sheets can gradually darken from transparent to black when they are converted to r-GO, they can be used to achieve the ombre hairstyle by controlling their degree of reduction through chemical, thermal, and light based approaches.[27-30] A proof-of-concept is shown in FIG. 4A, where a bundle of hair strands was first coated with a GO/chitosan solution (0.25 wt. %), followed by UV irradiation to reduce GO. Photomasks were used to control the exposure time of different parts of the hair to generate a gradient of shades from blonde to dark brown, corresponding to gradually decreased lightness (FIG. 4B). More rapid darkening can be achieved by using a higher intensity of UV light, or by applying chemical or thermal treatment based on various reduction mechanisms of GO.[27-30] On the other hand, since GO sheets absorb strongly UV light,[25,26] GO-based coatings can also serve as a light colored UV block to protect hair from irradiation damage, as well as a colorimetric indicator of the accumulative dose of UV exposure.

Discussion

In many engineering applications using graphene-based coatings, the black color of graphene is usually not a desirable feature. Using graphene coating for hair dye turns this compromise into a significant advantage. Unlike many other graphene applications that rely on the use of highly conductive and structurally more perfect r-GO or graphene sheets, hair—or in extension fiber dyeing—is very tolerant to the variations in their structures and electrical properties. Graphene-based hair dyes can be formulated without hazardous additives or volatile components, and do not impart permanent chemical and structural changes of hair. Therefore, they are safer to use than molecular dyes. Compared to molecules or nanoparticles, GO- and graphene-based sheets with large micron-sized lateral dimensions are much less likely to penetrate the dermal barrier,[41-43] especially when they are in a polymer matrix such as the chitosan gel used in this Example.

Graphene-based hair dyes can be applied simply by spraying and combing, which helps to complete the dyeing process more quickly than molecular dyes. Yet the coloration is quite durable, which is already comparable to commercial permanent hair dyes. In addition to their main function of dark or gradient coloration, r-GO and GO based hair dyes offer a number of enhancements to hair properties, including better antistatic and heat dissipation performances as demonstrated above.

In addition to fashion and aesthetics, the new functionalities enabled by graphene hair dyes have other uses. For example, they could be applied to coat animal furs to reduce electrostatically induced irritation in livestock farming. Antistatic hair will be useful for the development of humanoid robots to reduce the level of static interruption to embedded electronics. Highly conductive hair strands may also be repurposed as in-situ electrodes to interface with skin or "dermal electronics",[47] or become functional elements in wearable devices. Finally, at the end of their use, graphene coated hair waste can be readily repurposed or converted to make energy storage or sensing devices.[48-50]

Additional Results

Figure 5:
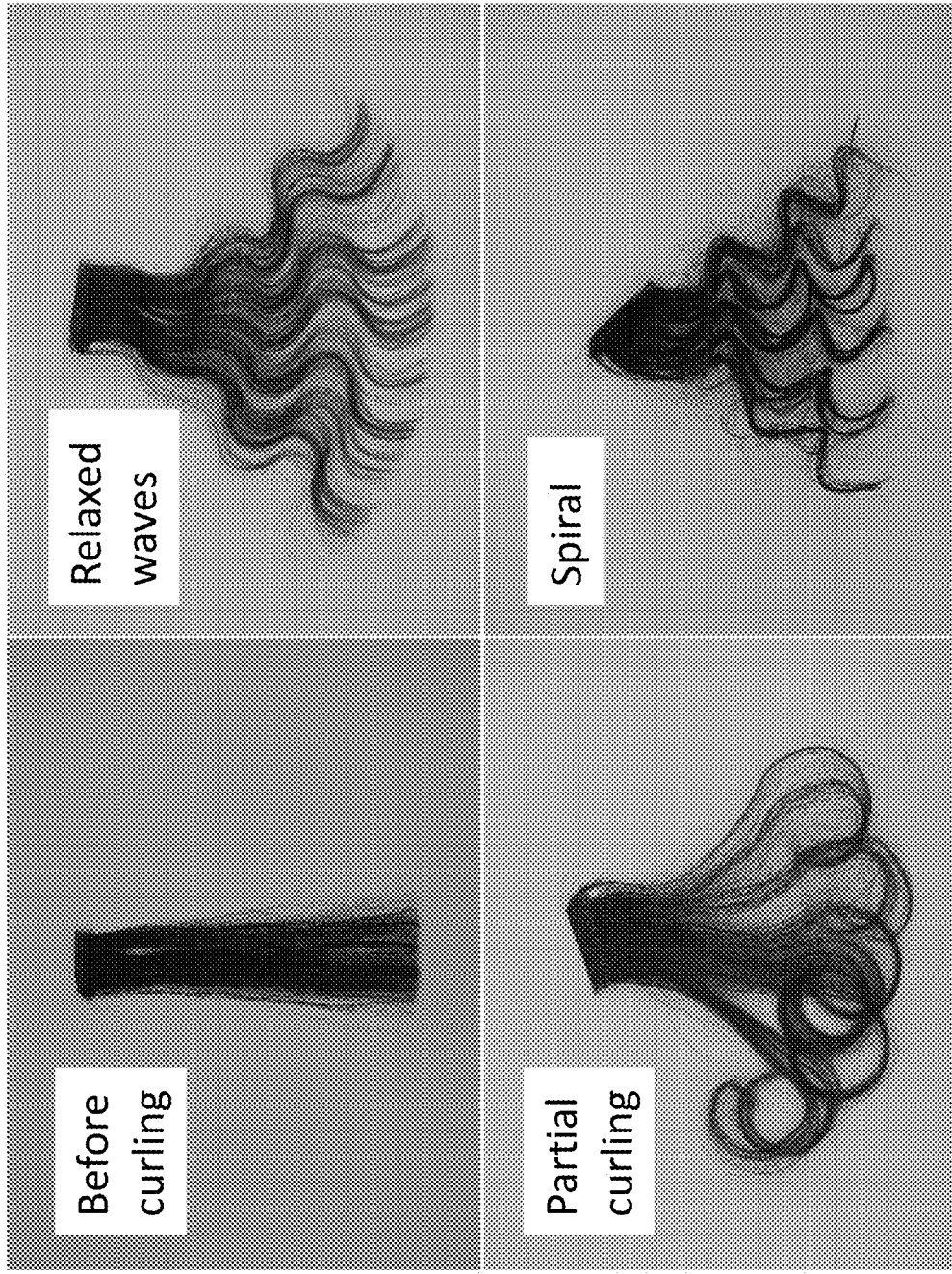
FIG. 5 demonstrates that graphene coated hair can fix the curvature of the coated hair without extra heat treatment or without applying small molecular chemicals.

The r-GO and GO hair dyes prepared as described above were applied to human hair samples as described above. However, prior to drying, the hair samples were curled. After curling, the hair samples were dried. The results shown in FIG. 5 demonstrate that the r-GO/GO coating can increase the bending stiffness of hair so as to fix its curvature. No extra heat treatment or chemicals are needed to change the chemical structure of the hair.

Figure 6:
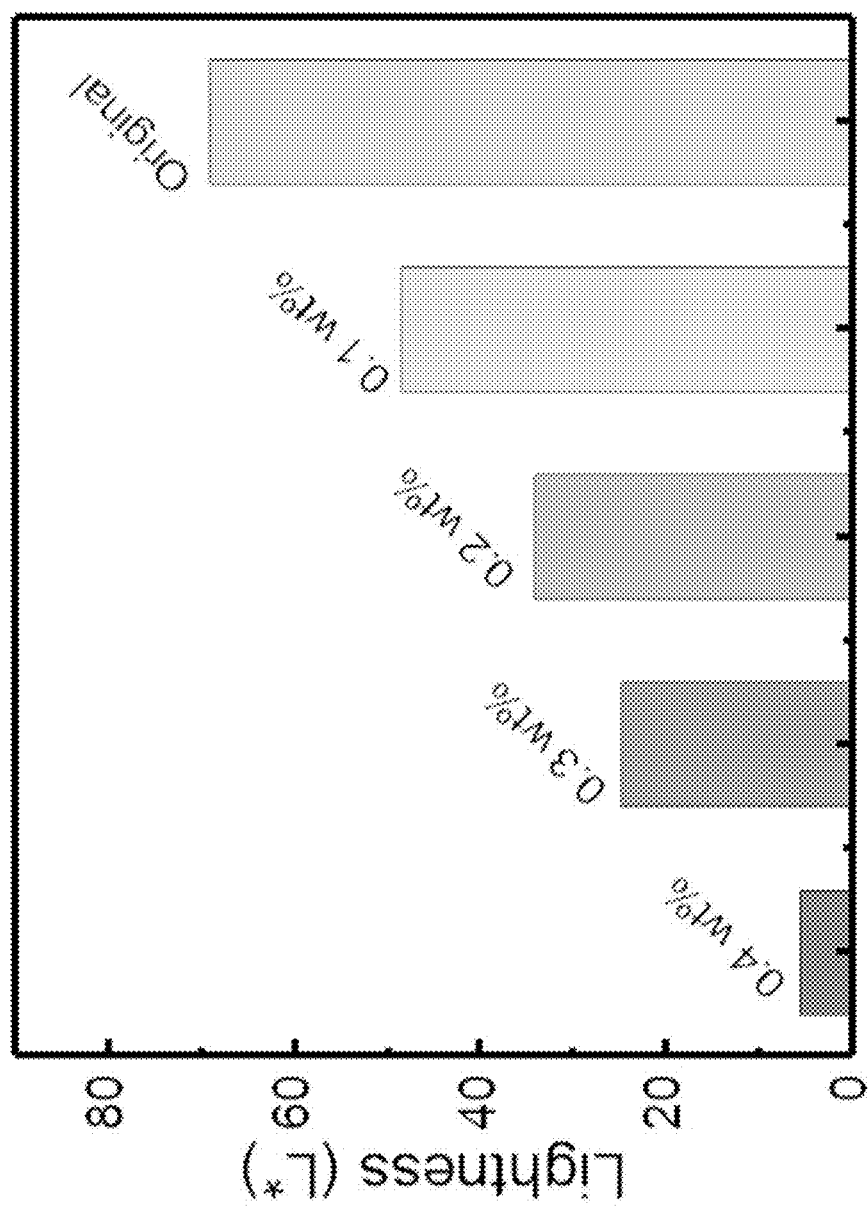
FIG. 6 shows the lightness of uncoated and graphene/polyaniline coated hair measured directly with a fiber optics spectrometer.

Hair dyes containing various amounts of polyaniline (PANI) and GO were prepared in water. Various relative amounts of PANI and GO were used, from 10:1 to 1:10, including 1:1. The relative amount of PANI and GO may be used to tune the color from blue (excess of PANI) to black (excess of GO). The hair dyes were applied to blonde human hair samples as described above. The treated blonde hair darkened (decreased L* values). FIG. 6 shows the lightness of uncoated and PANI/GO coated hairs (using compositions from 0.1 wt. % to 0.4 wt. % of PANI/GO), measured directly with a fiber optics spectrometer as described above. SEM images confirmed that the coating was uniform on individual strands of hair. The antistatic nature of the PANI/GO coated hair was also confirmed as described above (results similar to those shown in FIG. 2C). Finally, portions of PANI/GO coated hairs were "doped" with acid by exposing to an acidic vapor or solution (pH<6) to induce a color change of dark blue/black to green.

Hair dyes containing GO and molecular dye (either Rhodamine 6G or Coomassie Violet R200) in water or water/vitamin C/chitosan were prepared. The hair dyes were applied to blonde human hair samples as described above. The treated blonde hair darkened to either red (Rhodamine 6G) or purple (Coomassie Violet R200). Durability tests conducted as described above showed that the treated hair retained the red/purple color after multiple rounds of washing.

REFERENCES

1. Morel, O. J. X., and Christie, R. M. (2011). Current Trends in the Chemistry of Permanent Hair Dyeing. Chem Rev 111, 2537-2561.
2. Robbins, C. R. (2002). Chemical and physical behavior of human hair, 4th edn (New York: Springer).
3. Corbett, J. F. (1998). Hair Colorants: Chemistry and Toxicology (Micelle Press).
4. Sosted, H., Agner, T., Andersen, K. E., and Menne, T. (2002). 55 cases of allergic reactions to hair dye: a descriptive, consumer complaint-based study. Contact Dermatitis 47, 299-303.

5. McFadden, J. P., White, I. R., Frosch, P. J., Sosted, H., Johansen, J. D., and Menne, T. (2007). Allergy to hair dye. BMJ 334, 220.
6. Sosted, H., Johansen, J. D., Andersen, K. E., and Menne, T. (2006). Severe allergic hair dye reactions in 8 children. Contact Dermatitis 54, 87-91.
7. Kim, K. H., Kabir, E., and Jahan, S. A. (2016). The use of personal hair dye and its implications for human health. Environ Int 89-90, 222-227.
8. Nohynek, G. J., Fautz, R., Benech-Kieffer, F., and Toutain, H. (2004). Toxicity and human health risk of hair dyes. Food Chem Toxicol 42, 517-543.
9. Chung, K. T. (2016). Azo dyes and human health: A review. Journal of Environmental Science and Health Part C-Environmental Carcinogenesis & Ecotoxicology Reviews 34, 233-261.
10. Gago-Dominguez, M., Castelao, J. E., Yuan, J. M., Yu, M. C., and Ross, R. K. (2001). Use of permanent hair dyes and bladder-cancer risk. Int J Cancer 91, 575-579.
11. Takkouche, B., Etminan, M., and Montes-Martinez, A. (2005). Personal use of hair dyes and risk of cancer—A meta-analysis. Jama-Journal of the American Medical Association 293, 2516-2525.
12. Cook, L. S., Malone, K. E., Dating, J. R., Voigt, L. F., and Weiss, N. S. (1999). Hair product use and the risk of breast cancer in young women. Cancer Causes & Control 10, 551-559.
13. Zviak, C. (1986). The Science of Hair Care (Taylor & Francis).
14. Walter, P., Welcomme, E., Hallégot, P., Zaluzec, N. J., Deeb, C., Castaing, J., Veyssière, P., Bréniaux, R., Lévêque, J.-L., and Tsoucaris, G. (2006). Early use of PbS nanotechnology for an ancient hair dyeing formula. Nano Lett 6, 2215-2219.
15. Huang, X., Kobos, R. K., and Xu, G. (2008). Peptide-based carbon nanotube hair colorants and their use in hair colorant and cosmetic compositions. U.S. Pat. No. 7,452, 528.
16. Giroud, F., and Favreau, V. (2004). Cosmetic composition for volumizing keratin fibers and cosmetic use of nanotubes for volumizing keratin fibers. U.S. patent application Ser. No. 10/455,499.
17. Bogaty, H., Brown, K., Loveless, N. P., and Wolfram, L. J. (1985). Process and composition for coloring hair with pigments. U.S. Pat. No. 4,559,057.
18. Kim, J., Cote, L. J., and Huang, J. X. (2012). Two Dimensional Soft Material: New Faces of Graphene Oxide. Acc Chem Res 45, 1356-1364.
19. Hummers, W. S., and Offeman, R. E. (1958). Preparation of Graphitic Oxide. J Am Chem Soc 80, 1339-1339.
20. Narayan, R., Kim, J. E., Kim, J. Y., Lee, K. E., and Kim, S. O. (2016). Graphene Oxide Liquid Crystals: Discovery, Evolution and Applications. Adv Mater 28, 3045-3068.
21. Zhu, Y., Murali, S., Cai, W., Li, X., Suk, J. W., Potts, J. R., and Ruoff, R. S. (2010). Graphene and graphene oxide: synthesis, properties, and applications. Adv Mater 22, 3906-3924.
22. Dreyer, D. R., Park, S., Bielawski, C. W., and Ruoff, R. S. (2010). The chemistry of graphene oxide. Chem Soc Rev 39, 228-240.
23. Kim, J., Cote, L. J., Kim, F., Yuan, W., Shull, K. R., and Huang, J. X. (2010). Graphene Oxide Sheets at Interfaces. J Am Chem Soc 132, 8180-8186.
24. Cote, L. J., Kim, J., Tung, V. C., Luo, J. Y., Kim, F., and Huang, J. X. (2011). Graphene oxide as surfactant sheets. Pure Appl Chem 83, 95-110.
25. Kim, J., Kim, F., and Huang, J. X. (2010). Seeing graphene-based sheets. Mater Today 13, 28-38.
26. Loh, K. P., Bao, Q., Eda, G., and Chhowalla, M. (2010). Graphene oxide as a chemically tunable platform for optical applications. Nat Chem 2, 1015-1024.
27. Krishnan, D., Kim, F., Luo, J. Y., Cruz-Silva, R., Cote, L. J., Jang, H. D., and Huang, J. X. (2012). Energetic graphene oxide: Challenges and opportunities. Nano Today 7, 137-152.
28. Zhang, J., Yang, H., Shen, G., Cheng, P., Zhang, J., and Guo, S. (2010). Reduction of graphene oxide via L-ascorbic acid. Chem Commun (Camb) 46, 1112-1114.
29. Ding, Y. H., Zhang, P., Zhuo, Q., Ren, H. M., Yang, Z. M., and Jiang, Y. (2011). A green approach to the synthesis of reduced graphene oxide nanosheets under UV irradiation. Nanotechnology 22, 215601.
30. Cote, L. J., Cruz-Silva, R., and Huang, J. (2009). Flash reduction and patterning of graphite oxide and its polymer composite. J Am Chem Soc 131, 11027-11032.
31. Yang, X. M., Tu, Y. F., Li, L. A., Shang, S. M., and Tao, X. M. (2010). Well-Dispersed Chitosan/Graphene Oxide Nanocomposites. ACS Appl Mater Interfaces 2, 1707-1713.
32. Bao, H. Q., Pan, Y. Z., Ping, Y., Sahoo, N. G., Wu, T. F., Li, L., Li, J., and Gan, L. H. (2011). Chitosan-Functionalized Graphene Oxide as a Nanocarrier for Drug and Gene Delivery. Small 7, 1569-1578.
33. Martin, A. J. P. (1941). Tribo-electricity in wool and hair. Proceedings of the Physical Society 53, 186-189.
34. Wypych, G., and Pionteck, J. (2016). Handbook of antistatics, Second edition. edn (Toronto: ChemTec Publishing).
35. Shahil, K. M. F., and Balandin, A. A. (2012). Thermal properties of graphene and multilayer graphene: Applications in thermal interface materials. Solid State Commun 152, 1331-1340.
36. Rouf, T. B., and Kokini, J. L. (2016). Biodegradable biopolymer-graphene nanocomposites. J Mater Sci 51, 9915-9945.
37. Cheng, Q. F., Jiang, L., and Tang, Z. Y. (2014). Bioinspired Layered Materials with Superior Mechanical Performance. Acc Chem Res 47, 1256-1266.
38. Rouse, J. G., and Van Dyke, M. E. (2010). A Review of Keratin-Based Biomaterials for Biomedical Applications. Materials 3, 999-1014.
39. Tanabe, T., Okitsu, N., Tachibana, A., and Yamauchi, K. (2002). Preparation and characterization of keratin-chitosan composite film. Biomaterials 23, 817-825.
40. Pillai, C. K. S., Paul, W., and Sharma, C. P. (2009). Chitin and chitosan polymers:
Chemistry, solubility and fiber formation. Prog Polym Sci 34, 641-678.
41. Schneider, M., Stracke, F., Hansen, S., and Schaefer, U. F. (2009). Nanoparticles and their interactions with the dermal barrier. Dermato-endocrinology 1, 197-206.
42. Bussy, C., Ali-Boucetta, H., and Kostarelos, K. (2013). Safety Considerations for Graphene: Lessons Learnt from Carbon Nanotubes. Acc Chem Res 46, 692-701.
43. Volkov, Y., McIntyre, J., and Prina-Mello, A. (2017). Graphene toxicity as a double-edged sword of risks and exploitable opportunities: a critical analysis of the most recent trends and developments. 2D Mater 4.
44. Zhao, J. M., Deng, B., Lv, M., Li, J. Y., Zhang, Y. J., Jiang, H. Q., Peng, C., Li, J., Shi, J. Y., Huang, Q., et al. (2013). Graphene Oxide-Based Antibacterial Cotton Fabrics. Adv Healthcare Mater 2, 1259-1266.

45. Amen, S. K., Ho, R., Jang, H. W., Tao, L., Wang, Y. H., Wang, L., Schnyer, D. M., Akinwande, D., and Lu, N. S. (2017). Graphene Electronic Tattoo Sensors. ACS Nano 11, 7634-7641.
46. Hu, W. B., Peng, C., Luo, W. J., Lv, M., Li, X. M., Li, D., Huang, Q., and Fan, C. H. (2010). Graphene-Based Antibacterial Paper. ACS Nano 4, 4317-4323.
47. Xu, S., Zhang, Y. H., Jia, L., Mathewson, K. E., Jang, K. I., Kim, J., Fu, H. R., Huang, X., Chava, P., Wang, R. H., et al. (2014). Soft Microfluidic Assemblies of Sensors, Circuits, and Radios for the Skin. Science 344, 70-74.
48. Yu, M., Li, R., Tong, Y., Li, Y., Li, C., Hong, J.-D., and Shi, G. (2015). A graphene wrapped hair-derived carbon/sulfur composite for lithium-sulfur batteries. J Mater Chem A 3, 9609-9615.
49. Yuan, W., Zhou, Q., Li, Y., and Shi, G. (2015). Small and light strain sensors based on graphene coated human hairs. Nanoscale 7, 16361-16365.
50. Sun, G., Zhou, L., Li, J., Tang, J., and Wang, Y. (2015). Human hair-derived graphene-like carbon nanosheets to support Pt nanoparticles for direct methanol fuel cell application. RSC Adv 5, 71980-71987.
51. Luo, J., Kim, J., and Huang, J. (2013). Material processing of chemically modified graphene: some challenges and solutions. Acc Chem Res 46, 2225-2234.
52. Schanda, J., ed. (2007). Colorimetry: Understanding the CIE system (Hoboken, N. J.: Wiley-Interscience).

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A method for treating a keratin-based substrate, the method comprising:
    applying a cosmetic composition to a keratin-based substrate to form a coating of the composition thereon, the composition comprising graphene oxide (GO), reduced graphene oxide (r-GO), or both as a graphene-based material, a water dispersible polymer, and water, wherein the composition does not comprise the water dispersible polymer covalently bound to the graphene-based material;
    drying the coated keratin-based substrate, wherein the keratin-based substrate is hair having a lightness (L*) value and wherein the amount of the GO, the r-GO, or both, is selected to provide the coated hair with a changed L* value; and
    exposing different regions of the coated hair to different amounts of UV radiation or heat to obtain different L* values in the different regions.
2. The method of claim 1, further comprising exposing the coated hair to UV radiation or heat, wherein the coated hair exhibits a changed L* value only after exposure to the UV radiation or the heat.
3. The method of claim 1, wherein the coating of the coated hair has an average thickness of at least 1 μm and the average thickness varies by no more than ±10% across the surface of the coated hair.
4. The method of claim 1, wherein the water dispersible polymer is a compound which is soluble in water below a pH of 7 but which is insoluble in water above a pH of 7.
5. The method of claim 1, wherein the water dispersible polymer comprises amine groups.
6. The method of claim 1, wherein the water dispersible polymer is chitosan.
7. The method of claim 1, further comprising a second type of dispersant.
8. The method of claim 7, wherein the second type of dispersant is an acid.
9. The method of claim 8, wherein the second type of dispersant is ascorbic acid.
10. The method of claim 1, wherein the composition further comprises a coloring agent.
11. The method of claim 1, comprising at least 0.01 wt. % of the GO, the r-GO, or both; from 0.1 to 5 wt. % of the water dispersible polymer; from 0 to 10 wt. % of a second type of dispersant; from 0 to 10 wt. % of a co-solvent; from 0 to 10 wt. % of a coloring agent; and the water.
12. The method of claim 11, consisting of the GO, the r-GO, or both; the water dispersible polymer; the water; optionally, the second type of dispersant; optionally, the co-solvent; and optionally, the coloring agent.
13. The method of claim 1, consisting of the GO, the r-GO, or both; the water dispersible polymer; the water; optionally, a second type of dispersant; optionally, a co-solvent; and optionally, a coloring agent.
14. The method of claim 1, wherein the water dispersible polymer is chitosan and the composition further comprises ascorbic acid.
15. The method of claim 14, wherein the composition further comprises a coloring agent.
16. The method of claim 13, wherein the water dispersible polymer is chitosan, the second type of dispersant is present and is ascorbic acid, and the coloring agent is present.
17. A method for treating a keratin-based substrate, the method comprising:
    applying a cosmetic composition to a keratin-based substrate to form a coating of the composition thereon, the composition comprising graphene oxide (GO), reduced graphene oxide (r-GO), or both as a graphene-based material, a water dispersible polymer, and water, wherein the composition does not comprise the water dispersible polymer covalently bound to the graphene-based material;
    drying the coated keratin-based substrate, wherein the keratin-based substrate is hair having a lightness (L*) value and wherein the amount of the GO, the r-GO, or both, is selected to provide the coated hair with a changed L* value; and
    curling the coated hair prior to drying.

* * * * *